United States Patent
Bellei et al.

(10) Patent No.: US 10,288,465 B2
(45) Date of Patent: May 14, 2019

(54) DIFFERENTIAL FLOW-METER FOR MEASURING THE WEIGHT LOSS IN HAEMODIALYSIS TREATMENTS

(71) Applicant: MEDICA S.p.A., Medolla (IT)

(72) Inventors: Marco Bellei, Medolla (IT); Davide Bagnoli, Medolla (IT); Luciano Fecondini, Medolla (IT)

(73) Assignee: MEDICA S.P.A., Medolla (IT)

( * ) Notice: Subject to any disclaimer, the term of this patent is extended or adjusted under 35 U.S.C. 154(b) by 241 days.

(21) Appl. No.: 14/762,391

(22) PCT Filed: Jan. 21, 2014

(86) PCT No.: PCT/IB2014/058447
§ 371 (c)(1),
(2) Date: Jul. 21, 2015

(87) PCT Pub. No.: WO2014/111908
PCT Pub. Date: Jul. 24, 2014

(65) Prior Publication Data
US 2015/0367053 A1    Dec. 24, 2015

(30) Foreign Application Priority Data
Jan. 21, 2013  (IT) ............. BO2013A0024

(51) Int. Cl.
| | | |
|---|---|---|
| *G01F 1/684* | (2006.01) |
| *G01F 1/69* | (2006.01) |
| *A61M 1/14* | (2006.01) |
| *A61M 1/36* | (2006.01) |
| *A61M 1/16* | (2006.01) |

(52) U.S. Cl.
CPC .............. *G01F 1/69* (2013.01); *A61M 1/14* (2013.01); *A61M 1/1647* (2014.02); *A61M 1/3663* (2013.01); *G01F 1/684* (2013.01); *G01F 1/6845* (2013.01); *A61M 2205/3393* (2013.01)

(58) Field of Classification Search
None
See application file for complete search history.

(56) References Cited

U.S. PATENT DOCUMENTS

| | | | |
|---|---|---|---|
| 2,946,220 A | | 7/1960 | Cogniat et al. |
| 4,612,895 A | * | 9/1986 | Kuroiwa ................ F02D 43/00 123/494 |
| 4,781,068 A | * | 11/1988 | Pradelli ................ G01F 1/8477 73/196 |
| 5,861,555 A | | 1/1999 | Sture et al. |
| 7,347,092 B1 | * | 3/2008 | Ross ....................... G01F 1/684 73/204.25 |

(Continued)

FOREIGN PATENT DOCUMENTS

| | | | | |
|---|---|---|---|---|
| DE | 10 2011 002947 | | 1/2012 | |
| WO | WO-9849523 A1 | * | 11/1998 | ............. G01B 13/00 |

OTHER PUBLICATIONS

International Search Report with Written Opinion for PCT/IB2014/058447 dated Apr. 8, 2014.

(Continued)

*Primary Examiner* — Daniel J Colilla
(74) *Attorney, Agent, or Firm* — Workman Nydegger

(57) ABSTRACT

A differential flow-meter for measuring the weight loss in dialysis treatments. The differential flow-meter is of the "thermal anemometer" type.

5 Claims, 4 Drawing Sheets

(56) References Cited

U.S. PATENT DOCUMENTS

| | | | | |
|---|---|---|---|---|
| 2002/0077759 A1* | 6/2002 | Cohen | ............ | G01F 1/68 |
| | | | | 702/50 |
| 2004/0031331 A1* | 2/2004 | Blakley | ............ | A61M 15/009 |
| | | | | 73/862.52 |
| 2010/0274171 A1* | 10/2010 | Caleffi | ............ | A61M 1/3627 |
| | | | | 604/6.09 |
| 2012/0059305 A1 | 3/2012 | Akingba | | |
| 2012/0304731 A1* | 12/2012 | Lammerink | ............ | G01F 1/6845 |
| | | | | 73/1.16 |
| 2013/0075314 A1* | 3/2013 | Nikolic | ............ | A61M 1/14 |
| | | | | 210/143 |

OTHER PUBLICATIONS

Examination Report issued in EP Application No. 14710961.5 dated Nov. 23, 2018.

\* cited by examiner

DIFFERENTIAL FLOW-METER FOR MEASURING THE WEIGHT LOSS IN HAEMODIALYSIS TREATMENTS

CROSS-REFERENCE TO RELATED APPLICATIONS

The present invention is a 35 U.S.C. § 371 U.S. National Stage Application corresponding to PCT Application No. PCT/IB2014/058447, filed on Jan. 21, 2014, which claims priority to Italian Patent Application No. BO2013A000024, filed Jan. 21, 2013. The entire content of each of the aforementioned patent applications is incorporated herein by reference.

BACKGROUND OF THE INVENTION

1. Field of the Invention

The present invention concerns a differential flow-meter for measuring the difference of flow rate, or speed, between two fluids.

In particular, the present invention finds an advantageous application in the calculation of weight loss in haemodialysis treatments

2. Background

As already known, more than two million people in the whole world are presently affected by a chronic renal failure, with an annual growth rate close to 6%.

Currently, patients who do not undergo a kidney transplantation are treated by haemodialysis (or extracorporeal dialysis) or by peritoneal dialysis, which replaces the cleaning function of kidneys.

In both these treatments, blood is in contact with a special solution (called "dialysis fluid" or "dialysate") through a semipermeable membrane.

In haemodialysis, the blood purification takes place out of the body, inside a special filter, the dialyzer, whereas peritoneal haemodialysis uses the peritoneum natural membrane.

Through the semipermeable membrane, blood releases waste substances to the dialysate and yields/acquires ions by diffusion and convection, while the excess fluid (about two liters) is removed by ultrafiltration.

These processes take place using a computerized machine monitoring the total mass of liquid to be subtracted to the patient during the dialysis session, also called "weight loss".

The control system is programmed to achieve the goal of total removal of excess fluid at the end of the treatment (which usually lasts 4 hours).

This function is one of the most sensitive aspects of dialysis, since violent removal of liquids can cause significant side effects, such as, for instance, collapses and cramps.

Therefore, the control system of ultrafiltration must be made with the utmost accuracy.

Current systems of measurement of weight loss are all large and with high production costs, since they have to include several active elements.

U.S. Pat. No. 5,861,555 describes a differential flow-meter for measuring liquid flows for biomedical applications in dialysis machines. In this system, a certain number of temperature sensors is suitably connected in order to indirectly obtain the difference between the dialysate inlet flow and the dialysate outlet flow, with the help of a further non differential flow measurement relating to the flow rate of one or more of the channels. According to the adopted principle, the dialysis liquid is globally overheated at a temperature close to body temperature for reasons intrinsic to the dialysis treatment, and this overheating is then used to carry out the differential flow measurement as well.

Moreover, U.S. Pat. No. 2,946,220 describes a differential flow-meter for measuring gaseous fluids for chemical applications. In the claimed system, at least a pair of flow-meters working according to the calorimetric principle is suitably connected (Wheatstone bridge) in order to directly obtain a differential measurement of the respective flows. According to the calorimetric principle, a total number of six resistors, four of which are temperature sensors and two of which are heaters, are used and connected in a suitable way to obtain the aforesaid differential flow measurement.

For a better understanding of the present invention, FIG. 1 shows a schematic view of a differential flow-meter substantially working according to the "calorimetric principle" (calorimetric flow-meter). In other words, according to said known principle, it is measured the temperature variation of the previously overheated fluid at the place where the temperature sensor is arranged, said variation being induced by the flow rate or speed of the fluid itself.

For purely introductory purposes with regard to the present invention, reference will be made to the accompanying FIG. 1.

In said FIG. 1, 10 indicates, as a whole, a differential flow-meter working according to the "calorimetric principle".

The differential flow-meter 10, of known type, comprises a first separate channel 20 and a second separate channel 30 in which two fluids flow, said fluids being same or different.

The following devices are attached on the inner wall of channel 20:

heating means 21 of the fluid flowing according to an arrow (F1); the amount of heat supplied by the heating means 21 is controlled by a differential measuring device 40; the heating means 21 use the Joule effect to locally heat the fluid close to them; and temperature detecting means 22, placed close to the heating means 21; the temperature of said temperature sensor 22 being also detected by means of the differential measuring device 40.

Analogously, the following devices are attached on the inner wall of channel 30:

heating means 31 of the fluid flowing according to an arrow (F2); the amount of heat supplied by the heating means 21 is controlled by a differential measuring device 40; the heating means 21 use the Joule effect to locally heat the fluid close to them; and temperature detecting means 32 placed close to the heating means 31; the temperature of said temperature sensor 22 being also detected by means of the differential measuring device 40, which can also comprise a microprocessor processing system.

Furthermore, the differential measuring device can transform the instantaneous temperatures detected by the temperature sensors 22, 32 into differential flow rate or speed measurements of the two fluids passing in the two channels 20, 30.

For each channel, the temperature detecting means arranged close to the heating means can be formed by a single element, arranged downstream (as shown in FIG. 1) or upstream of the heating means (not shown), or can be formed by more elements, arranged both downstream and upstream (not shown). In all the aforesaid cases, the physical principle remains the same, and all the aforesaid means would still be monitored and measured by the differential measuring device 40.

BRIEF SUMMARY

The present invention develops a differential system directly measuring the difference between the two flows (weight loss) by using the principle of the "thermal anemometer" in order to obtain high sensitivity and precision and to guarantee the measurement accuracy.

This will lead to an accuracy of, at least, 5%, the tolerated limit being 10%. Inside the flow-meter, the inlet and the outlet flows will flow in two adjacent channels, having the same shape and size. A sensitive element can be found on the separating element arranged between the two channels, said sensitive element containing one or more resistors, self-heated thanks to the Joule effect, and directly measuring the difference of thermal dispersion between the two channels, related to the flow difference.

Main object of the present invention is therefore a differential flow-meter for biomedical applications in dialysis machines, having as an objective a highly accurate and precise differential measurement of the flow rate of dialysis fluids and the possible use of the machine where a dialysis treatment is needed, including typically hot places (e.g., operating room temperatures >30° C.).

The first objective can be reached by using a direct differential measurement (e.g., avoiding traditional flow measurements, namely of single channels, and subsequently using them for calculating their difference; or using them differently in calculations, thus avoiding a propagation of errors), and trying to reduce the sensor constructive complexity, thus minimizing the source of systematic and random manufacture errors. In the device object of the present invention, the optimal solution to these purposes is represented by a flow-meter based on the principle of the thermal anemometer, according to which a wire (resistor), specially overheated by the Joule effect, is cooled in proportion to the flow rate of the fluid touching it. The two (or four) resistors of the anemometer flow-meter are then configured as a Wheatstone bridge in order to obtain a direct differential measurement. Indicatively, the overheating is in the order of a few centigrade degrees. This method is an alternative to the more conventional calorimetric method seen in relation to FIG. 1, and therefore avoids having a separate heater and a separate temperature sensor. This implies a major constructive simplification, resulting in a limitation of the geometric nonidealities, thus obtaining greater measurement accuracy and precision. Moreover, the fact of having just one functional element implies a simplification in the control of the sensor, thus obtaining still the same advantage (simpler system, less error propagation).

The second objective can be reached by overheating only a negligible portion of the fluid. In fact, if the overheating functional to the flow measurement occurs only locally, close to the sensor, if necessary, it will be possible to implement a overheating, even relatively high, which, however, does not disrupt the overall temperature of the fluid. The use of a bypass, taking a small amount of fluid, could obviate the aforesaid problem, but has the disadvantage of introducing other sources of errors, thus limiting once again the accuracy and precision of measurement.

Therefore, according to the present invention, it is provided a differential flow-meter based on the principle of the "thermal anemometer" according to what defined in the attached independent claim, and preferably in any one of the claims directly or indirectly dependent on the aforesaid independent claim.

BRIEF DESCRIPTION OF THE DRAWINGS

For a better understanding of the present invention it will be now described a preferred embodiment, purely for non limitative purposes and with a reference to the attached drawings, in which.

DETAILED DESCRIPTION

Figure 2:
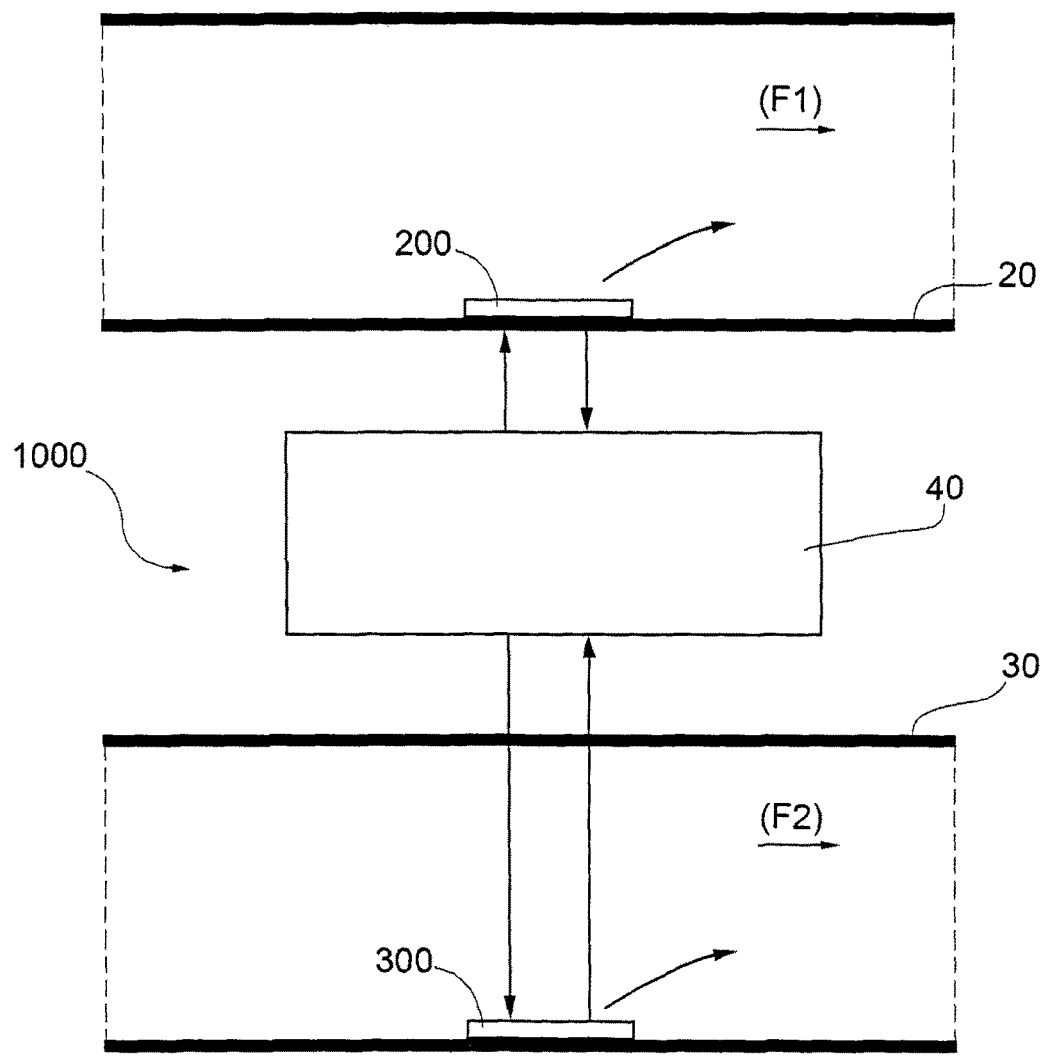
FIG. 2 shows a schematic view of a differential flow-meter made according to the present invention using the principle of the "thermal anemometer"

In FIG. 2 1000 indicates, as a whole, a differential flow-meter using the principle of the thermal anemometer flow-meter, which is one of the objects of the present invention.

The differential flow-meter 1000 comprises a first separate channel 20 and a second separate channel 30 in which two fluids flow, said fluids being same or different.

Figure 1:
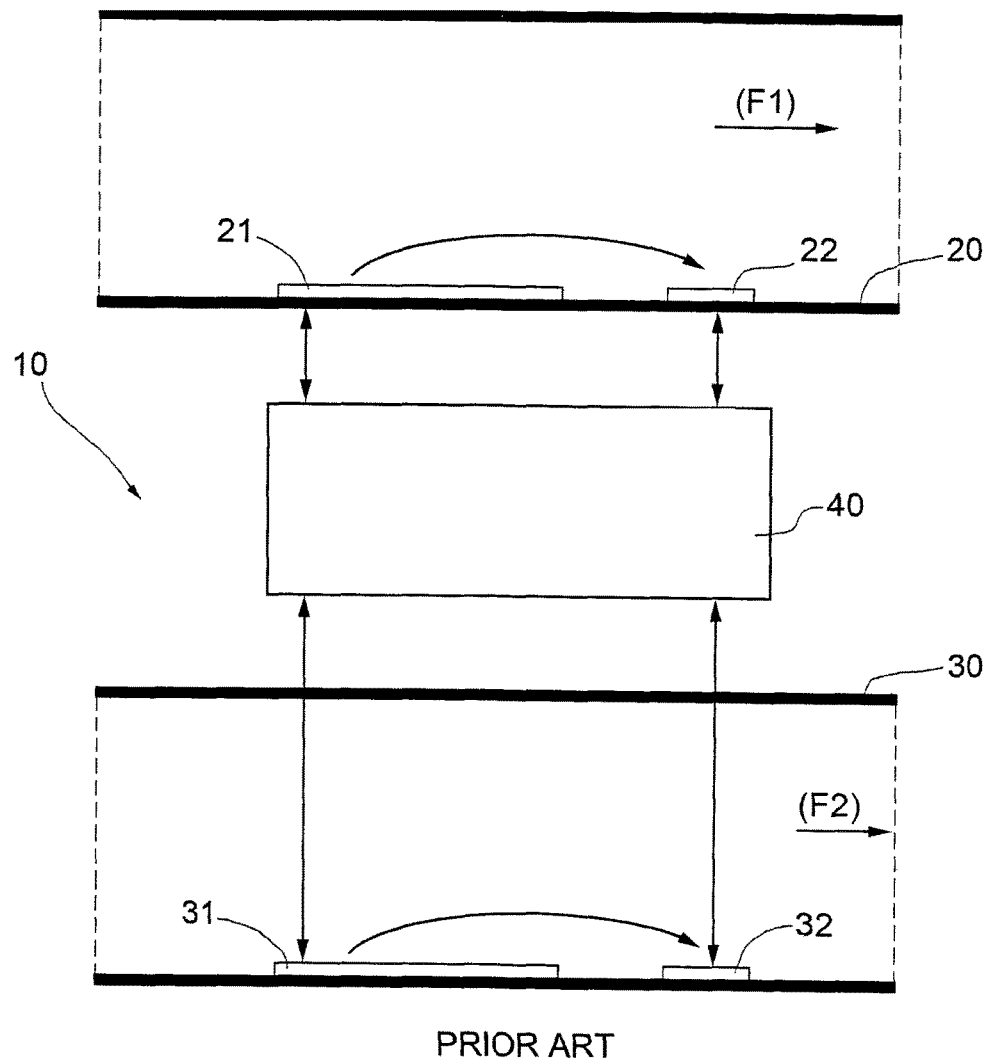
FIG. 1 shows a schematic view of a differential flow-meter using the "calorimetric principle"

A thermal device 200 is attached on the inner wall of channel 20. In said device 200, the temperature sensor 22 seen in FIG. 1 corresponds in principle to the heating plate 21. In particular, it is a resistor overheated thanks to the Joule effect, namely by imposing a suitably high current, with the resulting resistance increase, said resistor being cooled by the moving fluid, with the resulting temperature decrease. Therefore this resistance variation is inversely proportional to the fluid flow rate.

Analogously, a thermal device 300 is attached on the inner wall of channel 30. In said device 300, the temperature sensor 32 seen in FIG. 1 corresponds in principle to the heating plate 31.

In this way the variation of heat flow from the plate to the fluid can be measured by means of the differential measuring device 40.

Figure 3:
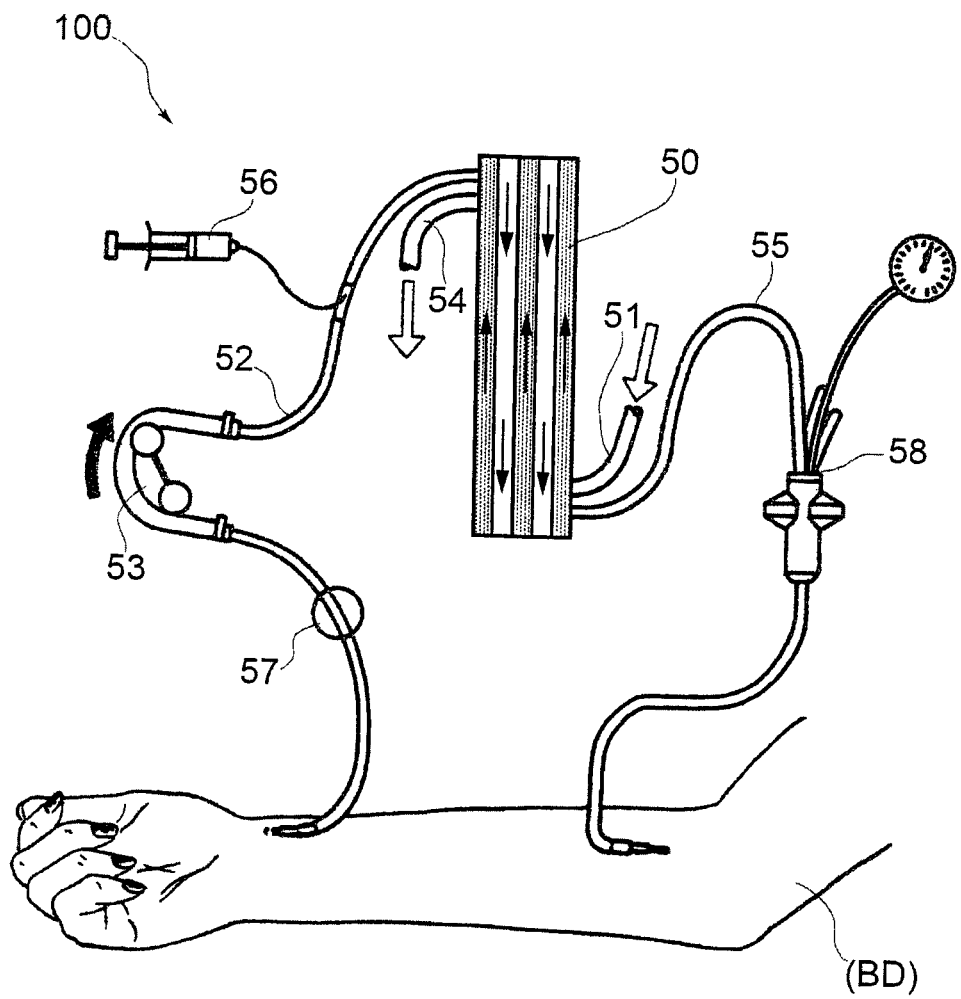
FIG. 3 shows a blood circuit of a haemodialysis machine to which it is applied a differential flow-meter according to the present invention.

In FIG. 3, 100 indicates, as a whole, a blood circuit of a haemodialysis machine (not shown in its entirety).

The blood circuit 100 comprises a dialyzer 50 fed, on the one side, by the dialysate through a duct 51 and, on the other side, by the arterial blood flowing through a duct 52 thanks to a peristaltic pump 53. The exchange of impurities between the blood and the dialysate takes place according to the previously described system.

The "dirty" dialysate exits the dialyzer 50 flowing in a duct 54, whereas the treated blood is re-introduced in the human body (BD) through a channel 55 connected to a patient's vein.

In a known way, in the duct 52 a certain amount of heparin is pumped into the arterial blood by means of a pumping device 56 in order to avoid blood coagulation.

The duct 52 is provided with a device 57 for measuring the arterial pressure. Analogously, the duct 55 is associated to a device 58 for measuring the venous pressure and for detecting the presence of unwanted air.

Figure 5:
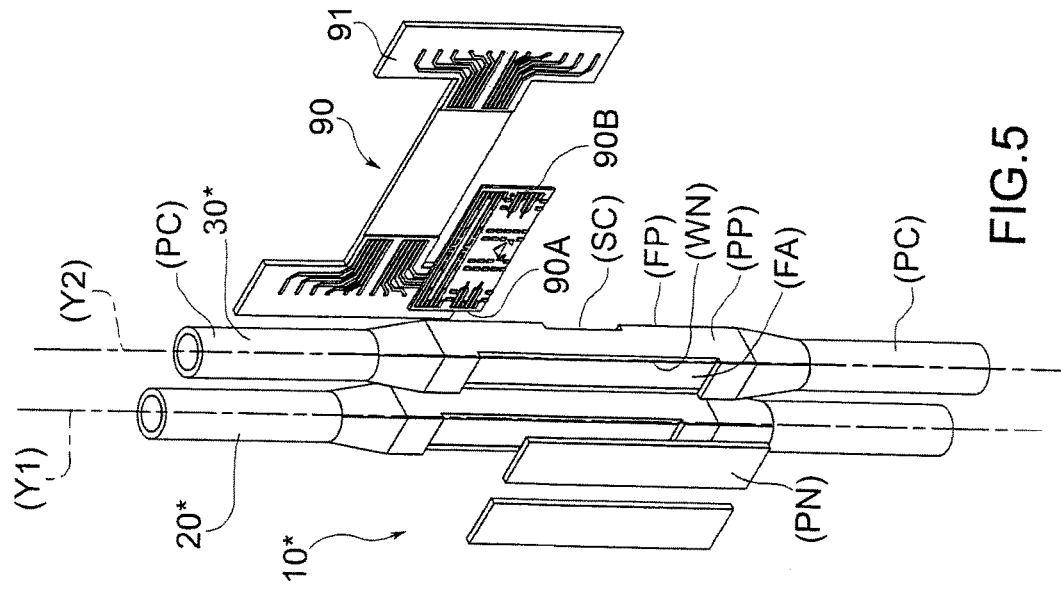
FIG. 5 shows an exploded view of the differential flow-meter of FIG. 4.
Figure 4:
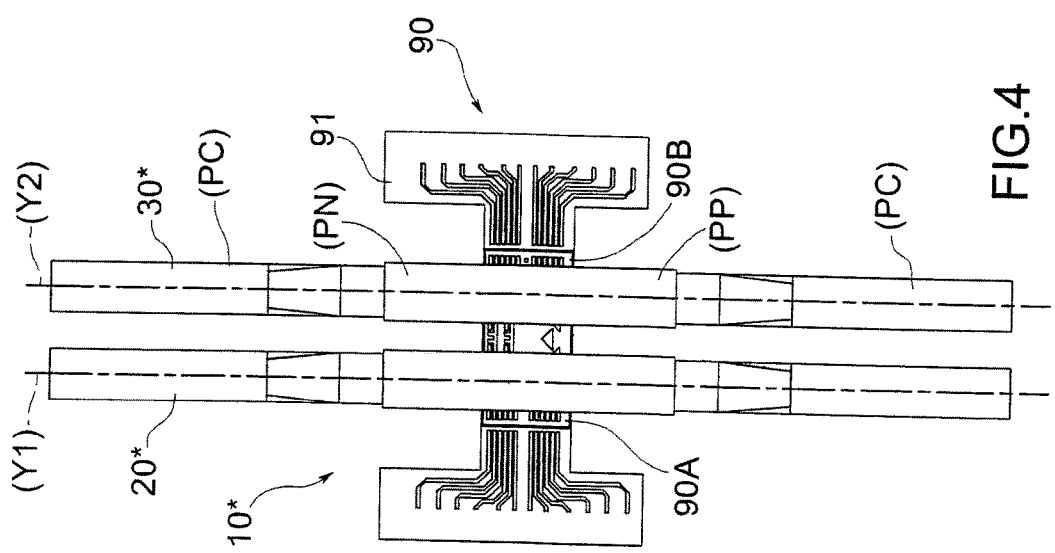
FIG. 4 shows a 3D view of the differential flow-meter whose components have been assembled.

FIGS. 4, 5 show a further embodiment of a differential flow-meter 10* object of the present invention.

The differential flow-meter 10*, 1000 can be connected to the ducts 51, 54 of the blood circuit 100 (FIG. 3) to calculate the so-called "weight loss", namely the liquid mass subtracted to the patient.

In an alternative embodiment, the person skilled in the art also finds obvious to connect the differential flow-meter 10*, 1000 to the two blood ducts 52, 55 (FIG. 3).

As shown in FIGS. 4, 5 the differential flow-meter 10* comprises two channels 20*, 30*.

In the embodiment shown in FIGS. 4, 5, channels 20*, 30* are identical, but they could also have different shapes.

Each channel 20*, 30* is aligned along a respective longitudinal symmetry axis (Y1), (Y2), which, in use, are parallel to each other.

In particular, channel 20* (but this obviously applies also for channel 30*) comprises two cylindrical end portions (PC) connected to a central prismatic portion (PP).

The two cylindrical end portions (PC) are used for the insertion of the remaining portions of the duct in which they are inserted (pair of ducts 51, 54; or, alternatively, pair of ducts 52, 55).

The central prismatic portion (PP), in turn, is provided with a flat back face (FP), on which a back groove (SC) is made, and a flat front face (FA) with an inspection window (WN), covered in use by a transparent panel (PN) (FIG. 5) to allow the visual inspection of the fluid flowing in said central prismatic portion (PP).

The back groove (SC) supports in use (FIG. 4) a micro-machined chip 90, advantageously made of silicon, integrating the thermal devices 200, 300 and the differential measuring device 40 seen in relation to the embodiment shown in FIG. 2.

More precisely, the chip 90 is glued and connected (for instance by means of the "wire-bonding" technique) to a substrate 91 (for instance a PCB, which stands for "Printed Circuit Board") containing all the electrical connections for data control and acquisition; the two channels on the substrate 91 bearing the two flows must have a suitable opening for housing the chip 90.

Once assembled, the differential flow-meter 10*, 1000 is as shown in FIG. 4.

In short, according to the preferred embodiment shown in FIGS. 4, 5, the present invention refers to a differential flow-meter 10*, 1000 for measuring the difference of flow rate, or speed, between two fluids.

The differential flow-meter 10* is identical to the differential flow-meter 100 shown in FIG. 2 and is characterized in that it comprises:
a) a first separate channel 20* and a second separate channel 30* in which two fluids flow, said fluids being same or different; and
b) a chip 90 located on either side of the two channels 20*, 30* so that a first portion 90A of the chip 90 is touched only by a first fluid flowing in the first channel 20*, and so that a second portion 90B of the chip 90 is touched only by a second fluid flowing in the second channel 30*.

Moreover, the chip 90 can measure and compare, by means of the method seen with regard to FIG. 2, any possible electrical resistance change in the first portion 90A and in the second portion 90B in order to calculate any possible change of flow rate or speed occurring in the fluids flowing in the two channels 20*, 30*.

The silicon micro-machining technology can be used to manufacture the sensitive portion of the differential flow-meter 10. This technology, starting from the silicon planar processing techniques, allows to create miniaturized planar and 3D structures, such as resistors resting on elastic membranes.

The silicon micro-machining techniques allow the manufacture of very small objects at low costs. Small size, combined with reduced costs and accuracy, allow the creation of dialysis machines which are cheaper, smaller, lighter and with lower operating costs. In particular, the operating costs are drastically reduced and, with no active element in motion, breakage and maintenance are rare and cheaper.

The objective of the device object of the present invention is the direct measurement of the difference of (mass or volume) flow rate, or speed, between two separate channels bearing the two flows.

The fluids forming the two flows can have same or different chemical composition, and can have same or different physical conditions (for instance density, temperature, speed, pressure).

The sensitive elements are connected and controlled in such a way to be directly affected by the difference of the two flows in question. A Wheatstone bridge connection can be used to this purpose, so that the measurement of the unbalance of the Wheatstone bridge is proportional to the flow difference in the two channels.

It should be noted that the measurement in question cannot ignore the fluid temperature, which must therefore be known (measured by the sensor) and suitably balanced.

The sensor manufacture comprises two steps:
1. micro-machining of silicon chips, containing all necessary sensitive elements and heaters; and
2. assembling of the aforesaid chip with other functional parts (substantially PCBs and fluidic channels), in order to obtain a flow sensor which can be used under desired thermal, fluidic and electrical conditions.

In short, the micro-machining consists in the creation of a suitable network of resistors, electrically insulated with regard to the fluid and thermally insulated with regard to the substrate. Indicatively, the manufactured resistors have a micrometer-sized section and a millimeter-sized length.

The sensor assembly can be carried out as follows. The chip bearing the sensitive elements configured in a differential manner is glued and connected (for instance by means of wire-bonding) to a substrate (for instance PCB) having all electrical connections for data control and acquisition; the two channels bearing the two flows must have a suitable opening for housing the chip.

In a second alternative embodiment (not shown), the two channels of the differential flow-meter are formed in at least one block, one face of which is closed by a layer of suitable material (e.g. silicon) on which the elements 200, 300 and the differential measuring device 40 are formed.

In a third embodiment, the sensitive elements (thermoresistances) are made by means of thermopiles or thermistors.

The main advantages of the differential flow-meter of the present invention are as follows:
high sensitivity and resolution;
reduced size;
low production costs; and
better reliability over time.

What is claimed is:
1. A differential flow-meter comprising a first separate channel and a second separate channel in which two fluids flow, said fluids being same or different;
said first channel comprising the following devices:

a first thermal device that functions as a first heater means of the fluid flowing in the first channel, the amount of heat supplied by said first heater means being controlled by a differential measuring device, the first thermal device also functioning as a first temperature detector means, the temperature of said first temperature detector means being also detected by means of the differential measuring device; and said second channel comprising the following devices:

a second thermal device that functions as a second heater means of the fluid flowing in the second channel, the amount of heat supplied by said second heater means being controlled by said differential measuring device, the second thermal device also functioning as a second temperature detector means, the temperature of said second temperature detector means being also detected by means of the differential measuring device;

wherein said differential measuring device can transform the instantaneous temperatures detected by the temperature detector means into differential flow rate or speed measurements of the two fluids passing in the two channels, wherein said first and said second thermal devices are integrated in a micro-machined chip.

2. The differential flow-meter according to claim 1, wherein each channel comprises
cylindrical end portions (PC) connected to a central prismatic portion (PP).

3. A Haemodialysis machine comprising:
at least a differential flow-meter, the differential flow meter comprising:
a first separate channel and a second separate channel in which two fluids flow, said fluids being same or different;
said first channel comprising the following devices:
a first thermal device that functions as a first heater means of the fluid flowing in the first channel, the amount of heat supplied by said first heater means being controlled by a differential measuring device, the first thermal device also functioning as a first temperature detector means, the temperature of said first temperature detector means being also detected by means of the differential measuring device; and
said second channel comprising the following devices:
a second thermal device that functions as a second heater means of the fluid flowing in the second channel, the amount of heat supplied by said second heater means being controlled by said differential measuring device, the second thermal device also functioning as a second temperature detector means, the temperature of said second temperature detector means being also detected by means of the differential measuring device;
wherein said differential measuring device can transform the instantaneous temperatures detected by the temperature detector means into differential flow rate or speed measurements of the two fluids passing in the two channels.

4. The Haemodialysis machine according to claim 3, wherein the two channels of said differential flow-meter are hydraulically connected to two ducts in which dialysate flows in order to calculate weight loss.

5. The Haemodialysis machine according to claim 3, wherein the two channels of said differential flow-meter are hydraulically connected to two ducts in which blood flows in order to calculate weight loss.

* * * * *